(12) United States Patent
Wintersperger et al.

(10) Patent No.: US 6,682,742 B1
(45) Date of Patent: Jan. 27, 2004

(54) VECTOR FOR INTEGRATION OF HETEROLOGOUS SEQUENCES INTO POXVIRAL GENOMES

(75) Inventors: Stefan Wintersperger, Icking (DE); Robert Baier, Oberschleissheim (DE); Gerd Sutter, München (DE); Marion Ohlmann, München (DE); Volker Erfle, München (DE)

(73) Assignee: GSF Forschungszentrum fur Unwelt und Gesundheit GmbH, Neuherberg (DE)

(*) Notice: Subject to any disclaimer, the term of this patent is extended or adjusted under 35 U.S.C. 154(b) by 0 days.

(21) Appl. No.: 09/980,029

(22) PCT Filed: May 25, 2000

(86) PCT No.: PCT/EP00/04786

§ 371 (c)(1),
(2), (4) Date: Dec. 26, 2001

(87) PCT Pub. No.: WO00/73476

PCT Pub. Date: Dec. 7, 2000

(30) Foreign Application Priority Data

May 28, 1999 (DK) .......................... 1999 00753

(51) Int. Cl.$^7$ .......................... A61K 39/285; C12N 7/01; C12N 15/863; C12N 15/39; C12N 5/10
(52) U.S. Cl. .......................... 424/199.1; 536/23.72; 424/232.1; 435/235.1; 435/320.1; 435/325; 435/456; 435/471
(58) Field of Search .......................... 435/320.1, 235.1, 435/325, 456, 471; 424/199.1, 93.2, 232.1; 514/44; 536/23.72

(56) References Cited

U.S. PATENT DOCUMENTS 5,185,146 A * 2/1993 Altenburger ............... 435/69.1
5,364,773 A * 11/1994 Paoletti et al. ............. 435/69.1
5,443,964 A   8/1995 Pickup et al.

FOREIGN PATENT DOCUMENTS

| EP | 0 261 925 | 3/1988 | |
| EP | 0261925 | * 3/1988 | ........... C12N/15/00 |
| WO | 96/39491 | * 12/1996 | ........... C12N/7/01 |
| WO | WO 97/02355 | 1/1997 | |
| WO | WO 98/13500 | 4/1998 | |
| WO | WO 98/56919 | 9/1998 | |

OTHER PUBLICATIONS

Characterization of the Vaccinia MVA Hemagglutinin Gene Locus . . . by Antoine et al., Gene 177 p. 43–46 (1996).
Mapping of Deletions in the Genome . . . by Meyer et al., Journal of General Virology(1991) 72, p. 1031–38.
Evaluation of the Thymidine Kinase . . . by Scheiflinger et al., Arch Virol (1996) 141, p. 663–9.
Novel Vaccinia Vector Derived From the Host Range . . . by Sutter et al, Dev. Biol. Stand. 1995, vol. 84, p. 195–200.
GenEmbl locus U94848/C, Vaccinia virus strain Ankara, complete genomic sequence, VRL Jan. 16, 1998.*
GenEmbl locus VACCG, vaccinia virus, complete genome (strain Copenhagen), VRL Aug. 3, 1993.*
Antoine et al (Virology 244:365–396, 1998)*
Panicali et al PNAS 80:5364–5368, 1983.*
Amegadzie et al, Virology 186:777–82, 1992, abstract only cited.*
Scheiflinger et al (Archives of Virology 143: 467–474, 1998).*
Jorg Schneider et al; Nature Medicine—vol. 4; Apr. 98; pp. 397–402; Enhanced immunogenicity for CD8+ T Cell . . . .
H. Meyer et al; Journal of General Virology (1991) 72; pp. 1031–1038; Mapping of deletions in the gemome of the . . . .

* cited by examiner

Primary Examiner—Mary E. Mosher
(74) Attorney, Agent, or Firm—Herbert Dubno; Jonathan Myers

(57) ABSTRACT

The present invention provides a DNA vector comprising a nucleic acid sequence useful for inserting heterologous sequences into the genome of poxviruses by homologous recombination. The present invention relates also, inter alia, to recombinant poxvirses carrying heterologous coding sequences transferred by the vector according to the present invention.

19 Claims, 2 Drawing Sheets

VECTOR FOR INTEGRATION OF HETEROLOGOUS SEQUENCES INTO POXVIRAL GENOMES

The present invention provides a new DNA vector comprising a nucleic acid sequence useful for inserting heterologous sequences into the genome of poxviruses by homologous recombination. The present invention relates also, inter alia, to recombinant poxviruses carrying heterologous coding sequences transferred by the vector according to the present invention.

BACKGROUND OF THE INVENTION

The successful worldwide eradication of smallpox via vaccination with live Orthopoxvirus, such as Vaccinia virus strain Western Reserve, Copenhagen or Ankara, stimulated in the early 80' research to study poxviruses in closer detail. Subsequently, said poxviruses were developed to well understood and easy-to-handle virus vectors or research tools, respectively (Moss, 1996). Today poxvirus vectors are used in various fields e.g. as expression vector or for the development of vaccines and therapeutic substances. The main reasons for the high acceptance of poxvirus vectors are the following promising features: Firstly, the vector viruses are easy to manipulate, are highly stable and cheap to manufacture. Secondly, said vector virus can accommodate large amounts of heterologous DNA and proofed to be a versatile expression vector. Thirdly, said vector virus is easily administered in vivo and succeeded in stimulating humoral and cellular immune responses. Accordingly, its use as a recombinant vaccine for protective immunisation against infectious disease or cancer made poxvirus vectors particularly attractive. Especially, Vaccinia virus, the best-known member of the Orthopoxvirus family, has been successfully used as recombinant vaccine to protect against diseases in a large variety of animal models (Carroll et al., 1997; Sutter et al., 1994a).

To develop and establish recombinant vaccinia viruses several insertion sites have been used. The most prominent insertion site of the vaccinia genome is the locus of the viral thymidine-kinase (tk) gene (Mackett et al., 1982). However, also other non-essential genes, such as the viral hemagglutinin and ribonucleotide reductase genes (Shida et al. 1987, Howley et al. 1996) or the naturally occurring deletion site II or III have been used to insert heterologous DNA sequences into the genome of vaccinia virus (Sutter et al., 1994a). Construction of recombinant vector viruses carrying several heterologous genes or several immunogenic epitopes becomes more and more of general interest. Accordingly, there is a high need to identify further sites in the virus genome, which are suitable to insert further heterologous DNA sequences.

Insertion of heterologous DNA sequences into a poxviral genome bears the risk to destroy regions essential for the virus propagation due to a lack of complete understanding of the poxviral lifecycle. Although the sequence information of several poxvirus genomes (Goebel et al. 1990; Antoine et al. 1998) is available the function of most proteins encoded by the identified open reading frames is not known. Accordingly, it is still a complicated challenge to identify sites in the genome, which are suitable to stably take up heterologous DNA without destroying any sequences essential for viral replication and propagation.

OBJECT OF THE INVENTION

It is thus an object of the present invention to identify a new insertion site in the poxviruses genome and provide vectors suitable to direct the integration of heterologous DNA sequences into said insertion site.

DESCRIPTION OF THE INVENTION

To achieve the foregoing and other objects, the present invention provides a vector comprising a nucleic acid sequence according to SeqID No. 1 or its complementary strand. The nucleic acid sequence according to SeqID No. 1 is highly homologous with parts of the genomic sequences of a poxvirus genome. Due to this homology the nucleic acid sequence according to the present invention is capable to initiate homologous recombination between said sequence and the corresponding genomic sequences of poxviruses. Thus, the present invention provides a mean useful to direct integration of DNA sequences into the genome of different orthopoxviruses, preferably into the genome of modified vaccinia virus Ankara (MVA), but also of further related orthopoxviruses such as, e.g., Vaccinia virus strain Western Reserve or Copenhagen.

According to a preferred embodiment the nucleic acid sequence of the present invention is derived from modified vaccinia Ankara virus (MVA), especially from MVA, which has been isolated and deposited on January $27^{th}$, 1994 according to the Budapest Treaty at the European Collection of Animal Cell Cultures (Salisbury, UK) under. Deposit No.: V94012707.

The present invention further provides a vector comprising nucleic acid sequences, which hybridise under stringent conditions to the sequences according to SeqIDNo: 1 or its complementary strand. In the context of this invention the term "vector" is understood as DNA vehicles of circular structure, such as plasmids, cosmids or artificial chromosomes. Said vector comprises in addition to the desired nucleic acid sequence regulatory sequences, selective marker genes and replicons enabling the autonomous replication of the vector. Hence, the vector according to the present invention can easily be amplified in and isolated from unicellular host organism. Furthermore, the term "under stringent conditions" defines parameters according to standard protocols (Sambrook et al., 1989), such as reaction temperature, formamide content or salt concentrations, which allow hybridisation of DNA—DNA sequences with a homology about and above 70%. As described above, also these sequences hybridising to the corresponding sequence of the poxvirus genome and are thus, particularly, useful to integrate heterologous sequences into a genome of orthopoxviruses.

Additionally, the present invention provides a vector comprising fragments of the above-mentioned nucleic acid sequence. These fragments comprise consecutive basepairs of said nucleic acid sequence and are also useful to integrate into the poxviral genome by homologous recombination. The length of said fragments is variable and fragments with only 30 basepairs being homologous to corresponding parts of the poxvirus genome are already sufficient to initiate recombination events. However, to increase the efficiency of homologous recombination between the poxvirus genome and the fragments as used in the present invention, said fragments are preferably about and above 200 basepairs in length, more preferably about and above 300 or 500 basepairs in length.

To initiate homologous recombination the vector according to the present invention and a wildtype poxvirus is introduced into a host cell. During replication of the poxvirus genome homologous recombination between the nucleic acid sequence inserted into the vector and the corresponding sequences of the poxvirus genome occurs. Since homologous recombination events occur only with a statistical probability of $1:10^3$ to $1:10^4$ any resulting recombinant poxvirus needs to be isolated. For this, e.g. a marker gene with functionally associated regulatory element is inserted into a cloning site of the, nucleic acid sequence included in the vector. After homologous recombination the resulting recombinant poxviruses are isolated by screening for expression of said marker gene or by selection for the expression of a dominant-selection marker gene, respectively.

According to a further embodiment the vector of the present invention is particularly useful for insertion of a desired heterologous coding sequence into a poxviral genome. The term "heterologous" is used in the context of this invention for any combination of nucleic acid sequences that is not normally found intimately associated in nature. The heterologous genes according to the present invention are preferably selected from the group of marker genes, therapeutic genes, such as anti-viral genes, anti-tumour genes, cytokine or chemokine genes, suicide genes, but also from host range genes or immunogenic epitopes. For insertion and/or expression of a desired heterologous coding sequences into a poxviral genome said heterologous coding sequence is inserted at a cloning site within the nucleic acid sequence.

In general, a cloning site is a restriction enzyme recognition site. According to the present invention the preferred cloning site for the insertion of heterologous sequences is the restriction enzyme recognition site of the EcoRI enzyme. This EcoRI site is unique in the nucleic acid sequence of the present invention, and is located between the two ORFs included in said nucleic acid sequence (FIG. 1). Beside this, any further restriction enzyme recognition site, which is located in the non-coding regions between said two ORFs can be used as cloning site. Surprisingly, also any cloning site located in one of the ORFs can be used for the insertion of heterologous sequences. Particularly, the inventors found that the destruction of said ORFs by such insertion into the ORFs does not hamper the viral life cycle or replication efficiency, respectively. Additionally, it was found by the inventors that the use of fragments according to the invention, which are incorporated in the vector to initiate homologous recombination, likewise did not interfere with viral propagation or replication efficiency.

Generally, heterologous sequences to be integrated into a viral genome by homologous recombination are flanked on both ends by sequences being homologous to corresponding sequences of the viral genome. However, the present invention also includes vectors wherein the heterologous sequence is only flanked on one side by the above-mentioned nucleic acid sequence. According to the present invention also vectors comprising only one fragment and a desired heterologous sequence are useful to insert said heterologous sequence into a poxvirus genome.

To guarantee expression of an inserted heterologous coding sequence at least one transcriptional control element is additionally inserted into the cloning sites. This transcriptional control element is in functional association with the heterologous coding sequence, thereby controlling and/or allowing its expression. According to a further preferred embodiment of the present invention the transcription control element is derived from a poxvirus and/or is a consensus sequence of a poxvirus derived transcription control element.

According to still a further embodiment of the present invention the vector comprises at least two recombinogenic sequences, which flank one or more heterologous coding sequences, particularly sequences encoding e.g. a marker or a host range gene, and/or the transcription control element(s) inserted into the cloning site. The term "recombinogenic sequences" describes nucleic acid sequences, which, due to their similar or nearly identical structure, are capable to delete any sequence between said recombinogenic sequences by intragenomic homologous recombination. Accordingly, the sequences flanked by said recombinogenic nucleic acid sequences are only transiently inserted into the viral genome and are, subsequently, completely deleted. This deletion of sequences flanked by recombinogenic sequences is of particular interest for the isolation of recombinant poxviruses, which should comprise only a heterologous coding sequence encoding a therapeutic or immunogenic gene, but no further marker or host range gene. For this, the marker gene, the host range gene and/or eventually also the transcription control element(s), but not the desired heterologous coding sequence, e.g. a therapeutic gene or immunogenic epitopes, are flanked by such recombinogenic sequences. After isolation of the recombinant virus, which is performed under a selection pressure upon the marker gene or the host range gene, the selection pressure is removed and thus, intragenomic homologous recombination to delete the marker or host range gene is allowed.

The present invention, furthermore, provides a recombinant poxvirus comprising in its genome the nucleic acid sequence transferred by the vector according to the present invention. Most preferably, this recombinant poxvirus is a recombinant MVA virus.

A further embodiment of the invention provides a method of treatment and/or prevention of an infectious disease or proliferative disorder. Said method comprises infection—either in vivo or in vitro—of a target cell population with recombinant poxviruses according to the present invention. Alternatively, according to this method the target cells are transduced—either in vivo or in vitro—with the vector according to the present invention and are infected, simultaneously or with a timelag, with any orthopoxvirus, included the recombinant poxvirus of the present invention. In this case, the poxvirus provides the cell with the poxviral replication and transcription machinery. As a consequence, the desired heterologous coding sequence incorporated in the vector and controlled by a poxvirus-derived transcriptional control element is expressed in the target cell. Target cells, which have been transduced or infected in vitro, can then according to the method of the present invention be applicated to a living animal body, including a human.

The invention provides the vector, the recombinant poxvirus and/or the target cells of the present invention useful for the treatment and/or prevention of an infectious disease or proliferative disorder. Furthermore, the vector, the recombinant poxvirus and/or the target cells according to the present invention are used for the production of a pharmaceutical composition, especially a vaccine, which is useful for in vivo and in vitro gene delivery and/or vaccination of mammals including humans, as described above.

SUMMARY OF THE INVENTION

The present invention, inter alia, comprises the following alone or in combination:

A vector for insertion of heterologous coding sequences into a poxviral genome, said vector including a nucleic acid sequence comprising one or more elements selected from the group consisting of:

(a) the nucleic acid sequence according to SeqID No. 1 or its complementary strand;

(b) a nucleic acid sequence which hybridizes under stringent conditions to the sequences as defined in (a);

(c) a fragment comprising at least 30 consecutive basepairs of the nucleic acid sequences as defined in (a) or (b);

the vector as above wherein the nucleic acid sequence is derived from a modified vaccinia Ankara virus (MVA);

the vector as above wherein additionally at least one transcriptional control element is included into at least one cloning site of said nucleic acid sequence;

the vector as above wherein the transcriptional control element is derived from a poxvirus genome or is the consensus sequence of a poxvirus derived transcriptional control element;

the vector as above additionally comprising at least one heterologous coding sequence, said heterologous coding sequence functionally associated with the transcriptional control element as above;

the vector as above wherein the heterologous coding sequence is selected from the group of marker genes, therapeutic genes, host range genes and/or immunogenic epitopes;

the vector as above comprising a recombinogenic sequence, which flanks one or more heterologous coding sequences encoding marker genes, host range genes and/or the transcriptional control element as above;

a recombinant poxvirus comprising in its genome the nucleic acid sequence transferred by the vector as above;

the recombinant poxvirus as above wherein the poxvirus is a modified vaccinia Ankara virus (MVA);

a method of introducing a heterologous sequence into poxvirus genome comprising (a) transduction of a host cell with the vector as above (b) infection of said host cell with a poxvirus, and (c) isolation of recombinant poxviruses;

a method of treatment and/or prevention of an infectious disease or proliferative disorder of a living animal body, including a human, comprising application to said living animal body the recombinant poxvirus as above, and/or the vector as above, or application of said vector with any other poxvirus; the method as above wherein the recombinant poxvirus is derived from an orthopoxvirus; a target cell comprising the recombinant poxvirus as above and/or the vector as above; the vector as above, the recombinant poxvirus as above and/or the target cell as above for the treatment and/or prevention of an infectious disease or proliferative disorder; the use of the vector am above, the recombinant poxvirus as above and/or the tar get cell as above for the production of a medicament for the treatment and/or prevention of an infectious disease or proliferative disorder; a pharmaceutical composition comprising the vector as above, the recombinant poxvirus as above and/or the target cell as above, and a pharmaceutical acceptable carrier and/or diluent; a pharmaceutical composition comprising the vector an above, a poxvirus, except the recombinant poxvirus as above, and a pharmaceutical acceptable carrier and/or diluent.

The following example will further illustrate the present invention. It will be well understood by a person skilled in the art that the provided example in no way may be interpreted in a way that limits the applicability of the technology provided by the present invention to this example, and the invention is therefore to be limited only by the full scope of the appended claims.

EXAMPLE 1

Construction of the Insertion Vector

To obtain sequences suitable for recombination into a poxviral genome, a DNA fragment derived from the modified vaccinia Ankara virus (deposited according to the Budapest Treaty under Deposit No.: V94012707 at the European Collection of Animal Cell Cultures in Salisbury, UK) was amplified by conventional PCR using the following oligonucleotide primers: A24R_1; 5'-CCGAAGCTTAATGAACGCCAGAGG-3', SeqID No.: 2; A27L_1c; 5'-AGGCTCGAGTAAGAGCGGCTATGAT-3', SeqID No.: 3.

Figure 1:
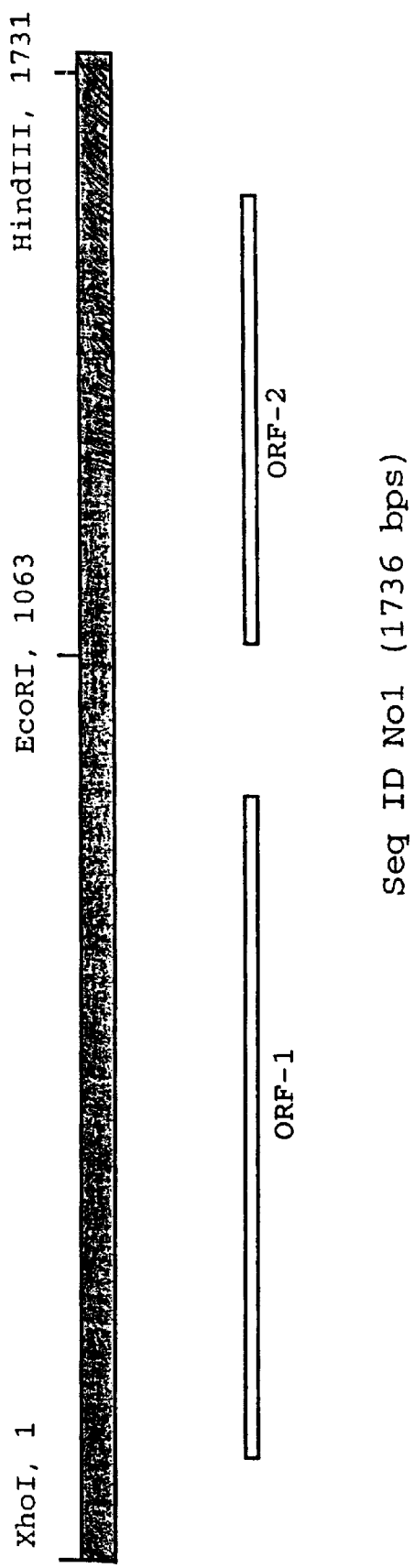
FIG. 1 in a map of the polynucleotide having Seq. ID No:1 with restriction sites xhoI.1, EcoRI, and Hind III and open reading frames ORF-1 and ORF-2.
Figure 2:
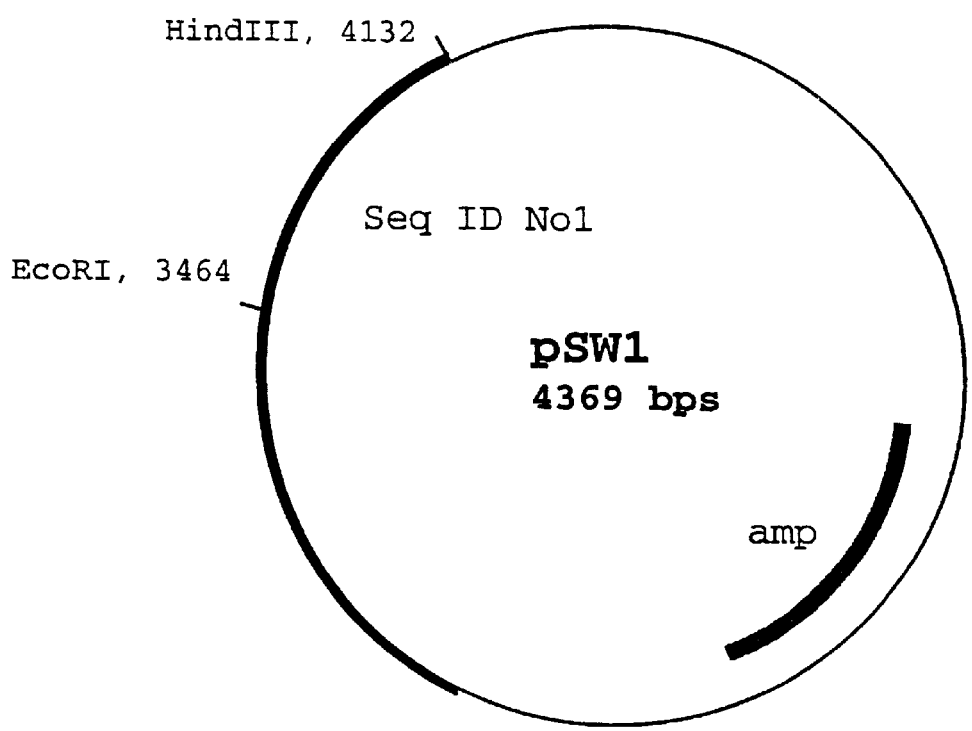
FIG. 2 is a map of plasmaid p8W1 comprising the polynucleotide having Seq. ID No: 1.

The oligonucleotide primers comprise, close to the 5' end and marked by underlining, a recognition sequence for the restriction enzymes HindIII (SeqID No.: 2) or XhoI (SeqID No.: 3) for subcloning of the resulting amplification product into a cloning vector. Accordingly, the specifically amplified sequence (SeqID No.: 1), which has a molecular weight of 1.7 kb, was subcloned SalI/HindIII into a pUC19 cloning plasmid (GenBank Accession No.: X02514). The resulting plasmid was designated pSW1 (FIG. 2).

The subcloned insert has been sequenced, and this sequence was compared to other known sequences from vaccinia virus strains Copenhagen, WR, and MVA. It was found that said sequence comprises parts of the sequence of the MVA-ATI region. The ATI gene of most orthopoxviruses form a dense cytoplasmic matrix embedding mature virions, so called inclusion bodies, which can be visualized by light microscopic examination of infected cells. Proposed ATI function is to provide higher stability and prolonged dissemination of infectious virus particles in the general environment. Among the orthopoxviruses are several members including ectromelia virus, cowpox virus and racoon poxvirus produce this typical inclusion protein with a size of 130 to 160 kDa. However, other members of the orthopox genus, as e.g. vaccinia virus Western Reserve (WR), vaccinia virus Copenhagen or MVA, form no such inclusion bodies. This is a result of sequence deletions or frame-shift mutations leading to loss of coding sequence and resulting in a truncated ATI-homologue. For example vaccinia virus WR expresses a 94 kDa ATI-homologue, while MVA and vaccinia virus strain Copenhagen expresses no such ATI-homologue.

For the further construction of insertion vectors, a naturally occurring recognition site of the restriction enzyme EcoRI was used to split the amplified sequence into two segments. These segments serve as flanking regions (flank1, flank2), that initiate homologous recombination with a poxvirus genome. In between these flanking regions, vaccinia virus promoter sequences—e.g. of the 7,5 promoter (7.5) and/or the synthetic promoter (sP)—as well as multiple cloning sites for the insertion of operably heterologous genes have been inserted. The resulting plasmids are designated pSW-7.5-sP, pSW-7.5, pSW-sP.

Additionally an expression cassette comprising the vaccinia virus host rage gene, K1L, fused to the EGFP fusion gene (isolated from the plasmid pEGFP, Clonetech, Gen- Bank Accession #: U76561) and the naturally occurring K1L promoter, was inserted between the flanking regions as described above. This expression cassette is especially helpful for efficient selection and isolation of recombinant viruses. The resulting plasmnid is designated pSWk1lgfp.

Generation of Recombinant Virus

For the generation of recombinant viruses 6-well tissue culture plates with cell monolayers of about 80% confluence are used. For the generation of recombinant MVA permnissive cells such as chicken embryo fibroblasts are used. For the generation of recombinant vaccinia viruses of the strain WR African Green Monkey (Vero) cells have been used.

Firstly, the cell culture medium is discarded and the cells overlaid with serum-free medium containing wild-type poxvirus at a multiplicity of infection (MOI) of 0.01 (e.g. an inoculum $5 \times 10^3$ IU (infectious units) in 1 ml medium for one well with $5 \times 10^5$ cells). This mixture is incubated for 1 hour at 37° C. in 5% $CO_2$-atmosphere. Then, the inoculum is removed and the cells are washed twice with 2 ml OptiMEM per well.

Subsequently, the cell monolayer is overlaid with Lipofectin/plasmid DNA-mix (total volume: 1 ml) prepared as described by the manufacturer (GIBCO BRL) and using 15 µg plasrnid DNA, of the pSWk1lgfp. The mixture is incubated for 5–12 hours at 37° C. in 5% $CO_2$-atmosphere. Then, the Lipofectin/plasmid DNA-mix is removed and the cells overlaid with 1.5 ml fresh medium supplemented with 10% FCS.

At 48 hours after infection, cell monolayer is detached with a cell scraper and the cells and medium are transferred into 2 ml-microcentrifuge tubes. The transfection harvest is stored at −20 to −80° C.

Upon transfection of the plasmid pSWk1lgfp into poxvirus infected cells, the host range gene K1L fused to the EGFP gene were precisely recombined into the site of the poxvirus genome, which is homologous with the flanking regions in the vector plasmid.

To isolate recombinant MVA viruses from non-recombinant MVA-viruses a host range cell, rabbit kidney (RK)13, was infected with virus material obtained from the transfection experiment as described above. Previous work had shown that MVA infection of rabbit RK13 cells results in an early block of viral replication characterised by impaired synthesis of intermediate viral RNA and lacking replication viral DNA. However, this non-productive MVA infection of RK13 cells could be overcome by coexpression of the vaccinia virus host range gene K1L (Sutter et al., 1994b). Accordingly, inoculation of virus material obtained from said transfection experiments into RK13 cultures resulted in the highly selective growth only of recombinant viruses, which coexpressed the K1L gene. After five consecutive passages on RK13 cells grown in 6-well or 96-well tissue culture plates the virus WVA-K1LGFP was isolated. The absence of non-recombinant MVA was demonstrated by PCR.

Additionally, the expression of the fused EGFP gene allowed a direct monitoring of infection with recombinant virus via GFP fluorescence. The direct monitoring is also used to identify and then isolate recombinant Vaccinia viruses of the strain WR, which are not sensitive to a K1L selection.

References:

Antoine, G. et al., 1998, The complete genomic sequence of the modified vaccinia Ankara strain: comparison with other orthopoxviruses. Virology, May 10;244(2):365–96.

Carroll, M. W. et al. 1997: Highly attenuated modified vaccinia virus Ankara (MVA) as an effective recombinant vector: A murine tumor model. Vaccine 15,387.

Fenner, F. et al. 1988: Smallpox and its eradication. World Health Organisation, Geneva.

Goebel, S J. et al., 1990, The complete DNA sequence of vaccinia virus. Virology, Nov;179(1):247–66, 517–63.

Howley, P M. et al., 1996, A vaccinia virus transfer vector using a GUS reporter gene inserted into the I4L locus. Gene, Jun 26;172(2):233–7.

Mackett, M. et al. 1982: Vaccinia virus: a selectable eukaryotic cloning and expression vector. *Proc. Natl. Acad. Sci. USA* 79, 7415.

Moss, B. 1996: Genetically engineered poxviruses for recombinant gene expression, vaccination, and safety. *Proc. Natl. Acad. Sci. USA* 93, 11341.

Sambrook, et al., 1989, Molecular Cloning: a laboratory manual, Cold Spring Harbor Laboratory Press publication, New York.

Shida, H. et al., 1987, Effect of the recombinant vaccinia viruses that express HTLV-I envelope gene on HTLV-I infection. EMBO J. Nov;6(11):337984.

Sutter, G. et al. 1994 a: A recombinant vector derived from the host range-restricted and highly attenuated MVA strain of vaccinia virus stimulates protective immunity in mice to influenza virus. Vaccine 12, 1032.

Sutter, G. et al. 1994b:Stable expression of the vaccinia virus K1L gene in rabbit cells complements the host range defect of a vaccinia virus mutant. J. Virol. 68, 4109.

What is claimed is:

1. A nucleic acid sequence including at least one cloning site and selected from the group consisting of:
   (a) a nucleic acid sequence according to Seq ID No. 1 or its complementary strand, and
   (b) a fragment comprising at least about 200 consecutive base pairs of the sequence defined in (a) including the ECORI site at position 1063 of SEQ ID NO:1.

2. The nucleic acid sequence according to SeqID No. 1 or its complementary strand as defined in claim 1.

3. A vector for insertion of a heterologous sequence into the ATI region of an orthopoxviral genome, said vector including a nucleic acid sequence selected from the group consisting of:
   (a) a nucleic acid sequence according to Seq ID No. 1 or its complementary strand, and
   (b) a fragment comprising at least about 200 consecutive base pairs of the sequence defined in (a) including the ECORI site at position 1063 of SEQ ID NO:1.

4. The vector according to claim 3 wherein the nucleic acid sequence includes at least one cloning site.

5. The vector defined in claim 4 wherein additionally at least one transcriptional control element is included in the cloning site of said nucleic acid sequence.

6. The vector defined in claim 4 wherein the cloning aito is the restriction site EcoRI.

7. The vector defined in claim 5 wherein the at least one transcriptional control element is obtained from a poxvirus genome or is a consensus sequence from a poxvirus genome.

8. The vector defined in claim 3 further comprising at least one heterologous sequence, said heterologous sequence functionally associated with the transcriptional control element thereof.

9. The vector defined in claim 8 wherein the heterologous sequence is selected from the group consisting of marker genes, therapeutic genes, host range genes and genes encoding immunogenic epitopes.

10. The vector defined in claim 8 comprising a recombinogenic sequence, which flanks one or more heterologous sequences on coding marker genes, host range genes, and or a transcriptional element thereof.

11. A recombinant orthopoxvirus having an ATI gene, comprising in its ATI gene region the nucleic acid sequence defined in claim 1 and an inserted hetorologous sequence.

12. The recombinant orthopoxvirus defined in claim 11 wherein the orthopoxvirus is selected from the group consisting of a modified vaccinia Ankara virus, vaccinia virus Western Reserve, and vaccinia virus Copenhagen.

13. The recombinant orthopoxvirus defined in claim 12 wherein the orthopoxvirus is the modified vaccinia Ankara virus.

14. A method of introducing a heterologous sequence into the ATI gene region of an orthopoxvirus having an ATI gene to obtain a recombinant orthopoxvirus which comprises the steps of:
   (a) transducing a host cell with a vector as defined in claim 3 comprising at least one heterologous sequence;
   (b) infecting said host cell with an orthopoxvirus having an ATI gene;
   c) inserting the heterologous sequence into an insertion site of the ATI gene of the orthopoxvirus by homologous recombination between the nucleic acid sequence and a corresponding genomic sequence of the orthopoxvirus to obtain a recombinant orthopoxvirus; and
   (d) isolating said recombinant orthopoxvirus.

15. The method of introducing a heterologous sequence into the gene region of the orthopoxvirus having an ATI gene defined in claim 14 wherein according to step (b) the orthopoxvirus is modified vaccinia Ankara virus.

16. A target cell comprising the recombinant orthopoxrirus having an ATI gene defined in claim 11.

17. A target cell comprising the vector defined in claim 3.

18. A pharmaceutical composition for effecting an immune response against an infectious disease or a proliferative disorder which consists essentially of a therapeutically effective amount of the recombinant poxirus as defined in claim 11, and in a form capable of producing an immune response against an infectious disease or a proliferative disorder in combination with a pharmaceutically acceptable inert carrier or diluent.

19. A method of effecting an immune response against an infectious disease or a proliferative disorder in an animal subject which comprises the step of administering to said subject a therapeutically effective amount of the pharmaceutical composition defined in claim 18.

* * * * *

SEQUENCE LISTING

<160> NUMBER OF SEQ ID NOS: 3

<210> SEQ ID NO 1
<211> LENGTH: 1736
<212> TYPE: DNA
<213> ORGANISM: Modified vaccinia Ankara virus
<220> FEATURE:

<400> SEQUENCE: 1

```
ctcgagtaag agcggctatg atatctctgg ctaaaaagat tgatgttcag actggacggc      60
gtccatatga gtaacttaac tcttttgtta attaaaagta tattcaaaaa atgagttata     120
taaatggcga acattataaa tttatggaac ggaattgtac caacggttca agatgttaat     180
```

-continued

| | | | |
|---|---|---|---|
| gttgcgagca | ttactgcgtt | taaatctatg atagatgaaa catggataa aaaaatcgaa | 240 |
| gcaaatacat | gcatcagtag | aaaacataga aacattattc acgaagttat tagggacttt | 300 |
| atgaaagcat | atcctaaaat | ggacgagaat agaaaatctc cattaggagc tccaatgcaa | 360 |
| tggctaacac | aatattatat | tttaaagaat gaatatcata agaccatgct agcgtatgat | 420 |
| aatggatcat | tgaatacaaa | atttaaaacg ttaaacattt atatgattac taacgttggt | 480 |
| caatatattt | tatatatagt | attttgtata atatctggta agaatcacga tggtactcct | 540 |
| tatatatacg | attctgagat | aacgagcaat gataaaaatc ttattaatga gcgtatcaag | 600 |
| tatgcatgta | agcaaatatt | acacggtcaa ttaactatag ctctgagaat tagaaataaa | 660 |
| ttcatgttta | taggatcacc | catgtattta tggtttaacg taaacggatc acaggtatat | 720 |
| cacgacatat | atgatcgtaa | tgccggtttt cataataaag agataggtag actactatac | 780 |
| gcatttatgt | actatctatc | tatctataag tggtagattt ttgaatgatt tcgcactatt | 840 |
| aaagtttacg | tatttaggag | aatcctggac atttagtttg agtgttcctg aatatatatt | 900 |
| atatggttta | ggatattctg | ttttcgatac tattgaaaaa tttagcaatg atgctatact | 960 |
| cgtttatgtt | agaacaaaca | atagaaatgg atatgattat gttgagttta ataaaaaagg | 1020 |
| aattgctaag | gtgacagaag | cctaaacccg ataacgataa gcgaattcat gctataagac | 1080 |
| gcatgaaggc | tgaacgtgaa | atcgctcgta aaaactgcgg aggtaaccca tgcgaacgtg | 1140 |
| aattgaaatc | tgaacgtagt | aacgtgaaga ggttggaata tcaactagat gctgagaaag | 1200 |
| aaaaagttaa | gttctacaaa | agagaactag aacgtgatcg gtatctttct agtagatatc | 1260 |
| ttacctcttc | ttcagatcca | catgagaaac cattaccaaa ttatacattt cctcgcatta | 1320 |
| aaaatgtatc | tccgttgaca | actgaggcta caggttctgt agaagtagca cctccatcca | 1380 |
| cagacgttac | cgaaccgatt | agtgatgtga ccatcggt ggatgtcgaa ccagaacatc | 1440 |
| ccccagcttt | ctgaatatca | gacttcagta tcccaagtag cagttacacc tccaccaaaa | 1500 |
| cctgaaactc | cacagatttt | cgaatatcag acgtccgatt ctatagttaa caatccacgc | 1560 |
| ccattttata | attcggatct | cgaatttgat gatattgata tgtatctact accaaactag | 1620 |
| aatattacac | cagaaaagac | ggcttgagat caactttatc taatggttta taaaacgaag | 1680 |
| gaggccttcg | ttcgaaatct | aatttgactt ttacgcctct ggcgttcatt aagctt | 1736 |

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
     oligonucleotide primer

<400> SEQUENCE: 2
ccgaagctta atgaacgcca gagg                                           24

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:
     oligonucleotide primer

<400> SEQUENCE: 3
aggctcgagt aagagcggct atgat                                          25